United States Patent [19]

Rees, Jr. et al.

[11] Patent Number: 5,516,945
[45] Date of Patent: May 14, 1996

[54] BIS(THIOLATE) COMPOUNDS OF GROUP II METALS

[75] Inventors: William S. Rees, Jr., Lithonia; Gertrud E. Kraeuter, Atlanta, both of Ga.

[73] Assignee: Georgia Tech Research Corporation, Atlanta, Ga.

[21] Appl. No.: 292,369

[22] Filed: Aug. 18, 1994

[51] Int. Cl.$^6$ .................................................. C07C 319/02
[52] U.S. Cl. .............................. 568/62; 556/10; 556/427
[58] Field of Search ................... 508/62; 556/10, 556/427

[56] References Cited

U.S. PATENT DOCUMENTS

| | | | |
|---|---|---|---|
| 3,431,239 | 3/1969 | Morris et al. | 568/62 |
| 4,255,561 | 3/1981 | Wood et al. | 568/62 |
| 5,168,540 | 12/1992 | Winn et al. | 385/128 |
| 5,213,844 | 5/1993 | Purdy | 556/112 |
| 5,306,836 | 4/1994 | Purdy | 556/112 |

FOREIGN PATENT DOCUMENTS

| | | |
|---|---|---|
| 1339456 | 10/1963 | France . |
| 5-208985 | 6/1994 | Japan . |

*Primary Examiner*—James H. Reamer
*Attorney, Agent, or Firm*—Oldham & Oldham Co.

[57] ABSTRACT

A new class of Group II bis(oligoetherthiolate) compounds is described for use in chemical vapor deposition processes in that it is volatile and soluble in common organic solvents, thereby rendering it suitable in the preparation of displays with full color, bright phosphors, which at present use ZnS-based technology. The drawback with ZnS is that the blue efficiency is too low. In another competing technology, $MGa_2S_4$-based materials, the sputtered films are amorphous, and the crystallization temperature is too high for inexpensive glass, thereby necessitating the use of expensive quartz. The instant invention secures the advantage of not depositing amorphous material in a two-step process. Rather a one-step process is used to get crystalline material directly, thereby providing a superior route to $MGa_2S_4$ in that it has the potential to give higher quality films at reduced cost.

8 Claims, 2 Drawing Sheets

5,516,945

BIS(THIOLATE) COMPOUNDS OF GROUP II METALS

TECHNICAL FIELD

The invention described herein pertains generally to a new class of Group II bis(oligoetherthiolate) compounds.

BACKGROUND OF THE INVENTION

Barium-containing compounds which have the potential to serve as sources in organometallic chemical vapor deposition are scarce. Initially reported over fifty years ago, organometallic barium moieties have received renewed attention in recent years, spurred in part, by the search for suitable precursors for employment in the preparation of barium-containing ceramic materials by chemical vapor deposition. In addition to this renewed interest in compositions containing barium-carbon bonds, other classes of reagents which have been examined include barium alkoxides, barium β-diketonates, and barium amides. Other less traditional barium-containing compounds would include $Ba(SiPh_3)_2$, $[Ba(P(SiMe_3)_2)2(THF)_2]_n$, and $Ba(P(SiMe_3)_2)_2 \cdot 4$ THF. Barium species containing covalent Ba-S interactions have not been studied in detail, perhaps due in part, to the assumption that ligands based on the soft sulfur atom are unsuited for the relatively hard barium ion. Barium is known to form complexes with dithiocarboxylic acids, however these compounds have a highly ionic character. Scant attention therefore, has apparently been paid to barium bis(thiolate) compounds.

The alkaline earth cations, particularly $Ba^{2+}$ portray a small charge/size ratio. The large ionic radius of barium demands high coordination numbers (8–12); however, its charge of +2 permits interaction with only two uninegatively-charged ligands, in order to preserve electroneutrality. Many barium compounds of the general formula $BaL_2$, therefore, reach coordinative saturation by oligomerization and/or catenation, or by solvent molecule incorporation. These compounds, in general, are involatile and insoluble, properties rendering them unsuitable for utilization in chemical vapor deposition. This challenge led to the design of ligands offering the potential for intramolecular stabilization, thereby inhibiting oligomerization.

One example of such a ligand is 2,2-dimethyl-8-methoxyoctane-3,5-dione. The deprotonated ligand forms a stable complex with barium and the resulting compound is a liquid at ambient temperature. A comparable ligand design has been applied to create intramolecularly-stabilized cyclopentadienide complexes of barium. Other examples of ligands offering the potential for intramolecular stabilization are oligoetheralcohols. Barium b/s(oligoetheralkoxide) compounds are liquids at ambient temperature and are monomeric in benzene solution, as determined by cryoscopy. These research efforts have now been extended in the area of intramolecularly-stabilized barium compounds to encompass a new class of compounds, i.e., Group II metal bis(oligoetherthiolates).

SUMMARY OF THE INVENTION

In accordance with the present invention, there is provided a new class of compounds, i.e., Group II metal bis(oligoetherthiolates).

It is an object of this invention to provide a novel composition-of-matter containing bis(thiolate) compounds of Group II metals.

It is another object of this invention to provide a method of synthesizing bis(thiolate) compounds of Group II metals.

It is still another object of this invention to provide a Group II metal-containing bis(thiolate) compound which can serve as a source in organometallic chemical vapor deposition.

It is still yet another object of this invention to provide a Group II metal-containing bis(thiolate) compound which can serve as a source in organometallic chemical vapor deposition which is volatile and soluble in common organic solvents.

It is a further object of this invention to provide a Group II metal-containing bis(thiolate) compound whose ligand is capable of intramolecular stabilization.

It is a further object of this invention to provide a Group H metal-containing bis(thiolate) compound whose ligand is capable of intramolecular stabilization and which is a liquid at ambient temperature.

These and other objects of this invention will be evident when viewed in light of the drawings, detailed description, and appended claims.

DETAILED DESCRIPTION OF THE DRAWINGS

The invention may take physical form in certain pans and arrangements of parts, a preferred embodiment of which will be described in detail in the specification and illustrated in the accompanying drawings which form a part hereof, and wherein:

FIG. 3b is a mass spectrum of the volatile products identified during the time period of 1.284 to 2.667 minutes in the gas chromatograph of FIG. 3a.

DETAILED DESCRIPTION OF THE INVENTION

Figure 1:
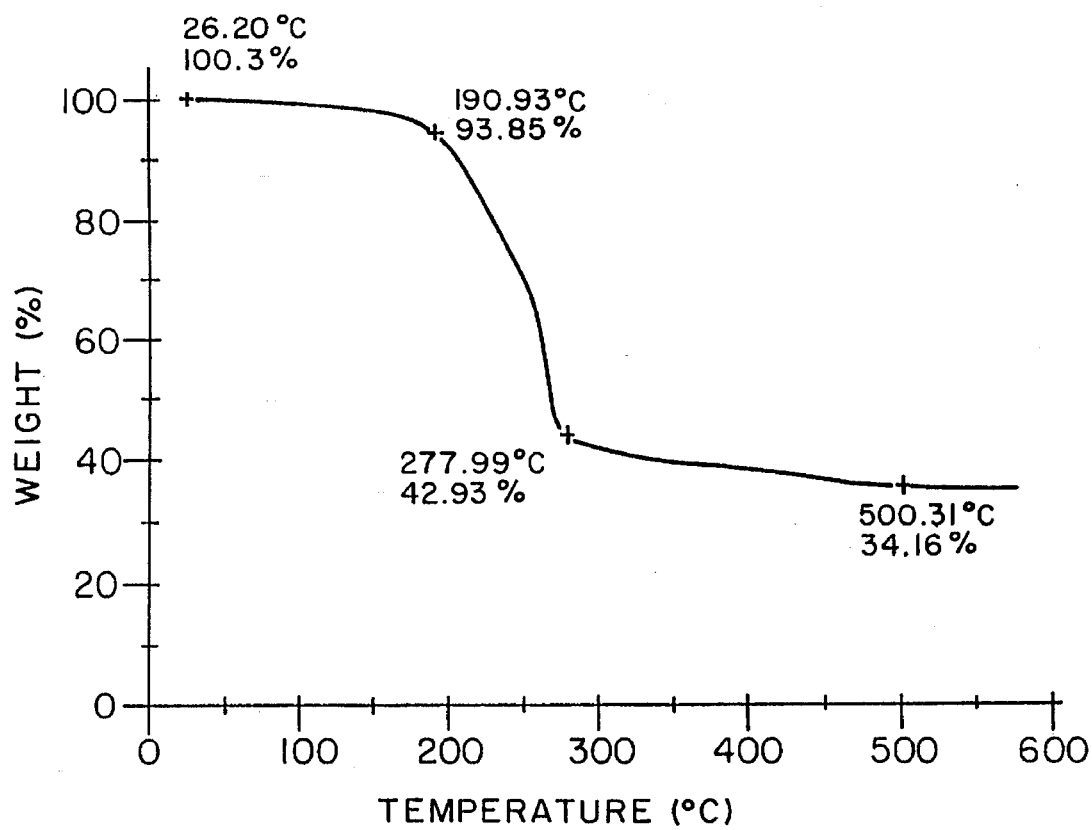
FIG. 1 is a thermal gravimetric analysis (TGA) of barium bis(2-(2butoxyethoxy)ethylthiolate)

Referring now to the drawings wherein the showings are for purposes of illustrating the preferred embodiment of the invention only and not for purposes of limiting the same, the Figures provide assistance in determining the characterization of one particular compound of the invention, i.e., barium bis(2-(2butoxyethoxy)ethylthiolate).

Metal thiolates have attracted interest in recent years as a class of compounds serving as unimolecular ;precursors for the low temperature synthesis of metal sulfides. Barium metal reacts with 2-(2-butoxyethoxy)ethanethiol in the presence of ammonia gas to form an air-sensitive viscous oil, which is soluble in typical organic solvents as shown below:

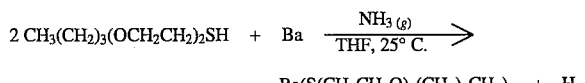

$$2 CH_3(CH_2)_3(OCH_2CH_2)_2SH + Ba \xrightarrow[THF, 25°C.]{NH_{3(g)}}$$

$$Ba(S(CH_2CH_2O)_2(CH_2)_3CH_3)_2 + H_2$$

The barium bis(2-(2-butoxyethoxy)ethylthiolate) is a dimer in benzene solution and believed m be of the general structure shown below:

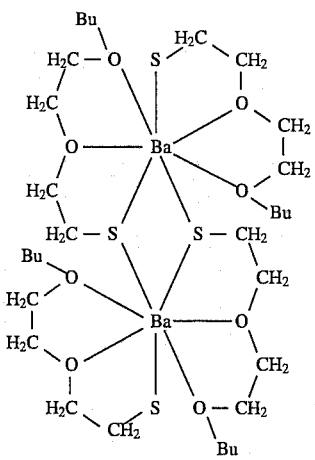

When the barium bis(2-(2-butoxyethoxy)ethylthiolate) was heated under vacuum at 220° C. for two hours, a complete conversion into crystalline barium sulfide was achieved, as determined by X-ray powder diffraction, and represented in the following equation:

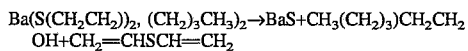

Thermogravimetric analysis indicates that barium bis(2-(2-butoxyethoxy)ethylthiolate) decomposes in a one-step thermolysis, commencing at 190° C. as shown in FIG. 1. The observed mass loss corresponds to the reduction predicted for the formation of BaS. One of the volatile products of the reaction is 2-butoxyethanol, as determined by GC/MS. The second volatile product, presumably, is divinylsulfide, however the volatility of the compound inhibited its isolation.

The best mode for carrying out the invention will now be described for the purposes of illustrating the best mode known to the applicant at the time. The examples are illustrative only and not meant to limit the invention, as measured by the scope and spirit of the claims.

Examples

Example #1 - Synthesis of 2-(2-butoxyethoxy)thiol

The compound 2-(2-butoxyethoxy)thiol was synthesized by the reaction of 2-(2-butoxy(ethoxy)ethylbromide) and thiourea according to the procedure of Urquhart, Gates, and Connor, Organic 3)rathesis, 21, (1941) pp36–38.

Example #2 - Synthesis of Barium bis(2-(2-butoxyethoxy)ethylthiolate)

A 2.67 g (15.0 mmol) sample of 2-(2-butoxyethoxy)thiol was added to 1.1 g (8.0 mmol) of elemental barium in 40 mL of THF. A stream of dry $NH_{3(g)}$ was bubbled through the reaction mixture for 40 min. The flow of $NH_{3(g)}$ was stopped and the mixture was stirred overnight at ambient temperature. Most of the barium had been consumed at this point. The mixture was filtered and the THF was removed under vacuum yielding a light yellow oil which was dissolved in 20 mL of toluene and filtered. After removal of the toluene under vacuum, an air-sensitive light yellow oil remained, with a yield of 3.0 g. Characterization data:

$^1$H-NMR(300 MHz, $CDCl_3$) δ=0.89 (t,3H), 1.37 (m,2H), 1.50 (m,2H), 2.70 t,2H), 3.30 (t,2H), 3.40 (s,2H), 3.56 (t, 2H).

$^{13}$C-NMR (75 MHz, $CDCl_3$) δ=13.6 ($\underline{C}H_3$), 19.0 ($\underline{C}H_2$), 31.5 ($\underline{C}H_2$), 69.3 ($\underline{C}H_2$), 70.0 ($\underline{C}H_2$), 70.3 ($\underline{C}H_2$), 71.0 ($\underline{C}H_2$), 71.2 ($\underline{C}H_2$).

IR (Nujol, NaCl plates, $cm^{-1}$) 2950, 1450, 1340, 1280, 1240, 1100, 950, 900, 730, 675.

TGA ($N_2$, 1 atm); Weight residue: 34.2% (obs. at 500° C.); 34.5% (calc. [BaS]).

Cryoscopy(benzene): compounds: 0.251 g solvent: 2.028 g freezing point: 5° C. (benzene) 4.4° C. (benzene+ compound)

Molecular Weight:

1056 g/mol (calculated from cryoscopy)

1031.24 g/mol (calculated for n=2 dimer)

Cryoscopic molar mass determination (benzene): $M_r$=1033, n=2.1.

C, H Analysis observed 39.56% C. 6.90%H calculated 39.12% C 6.98% H

Example #3-Thermolysis of Barium bis(2-(2-butoxyethoxy)ethylthiolate)

Figure 2:
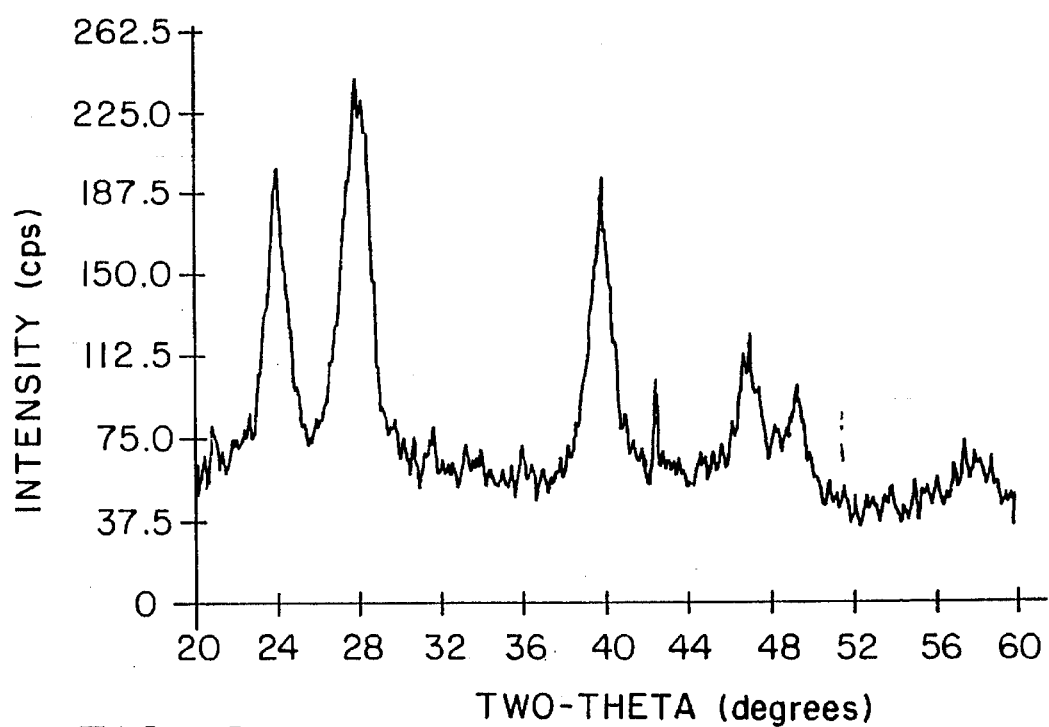
FIG. 2 is an XRPD of the thermolysis product from barium bis(2-(2butoxyethoxy)ethylthiolate)
Figure 3A:
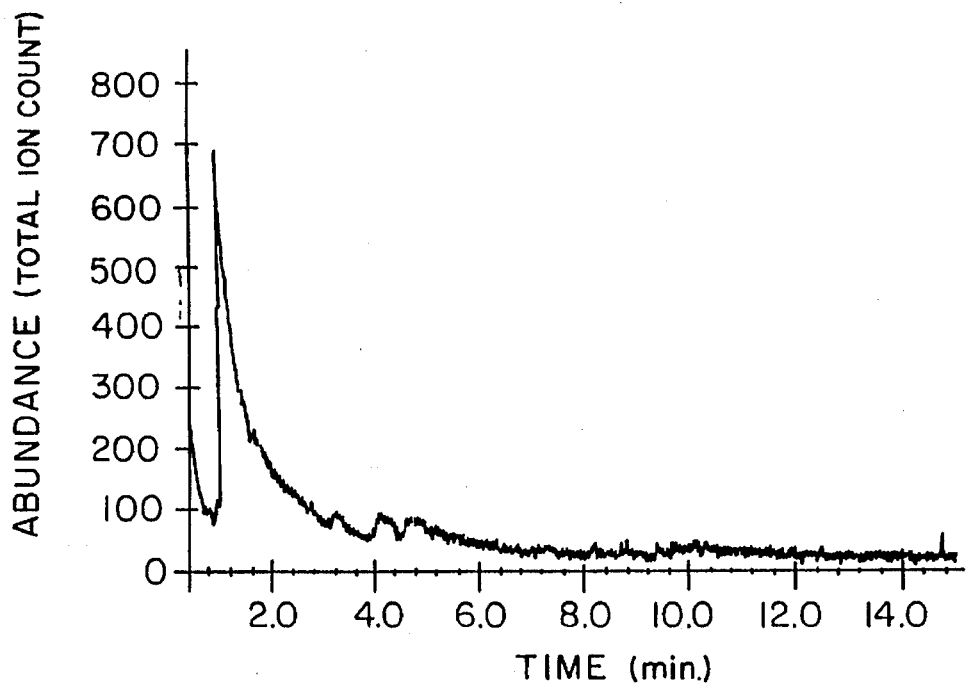
FIG. 3a is a gas chromatograph of concentration vs. time of the volatile products identified by the thermolysis of barium bis(2-(2butoxyethoxy)ethylthiolate)
Figure 3B:
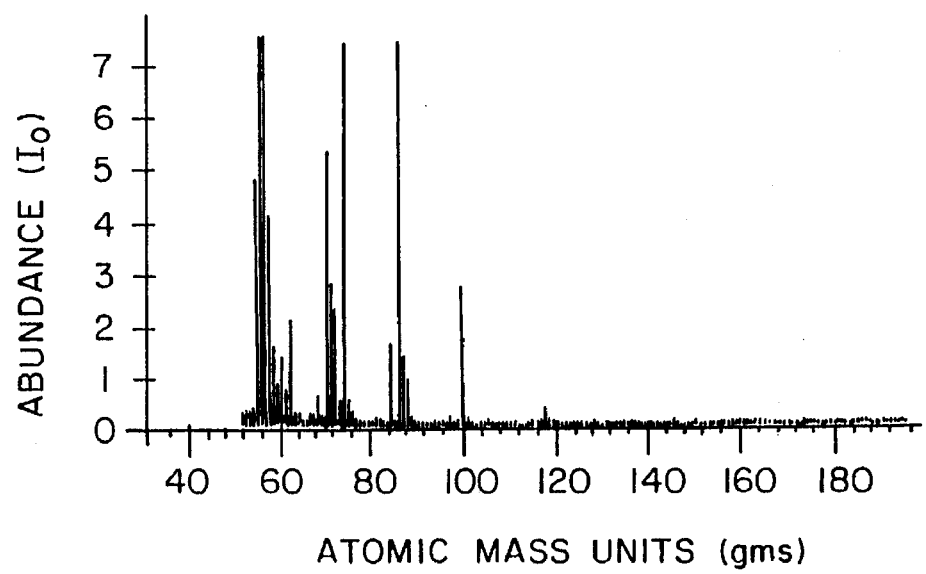

A sample of 0.3778 g of barium bis(2-(2-butoxyethoxy)ethylthiolate) was placed in a flask and heated to 220° C. under vacuum (0.1 Torr). A black solid remained (0.1504 g, 115% calculated for BAS). XRPD (FIG. 2) and SEM were used to characterize the product. The volatile products were identified by GC/MS, the spectra of which are shown in FIGS. 3a and 3b.

Discussion

One application for this class of novel compounds would lie in the preparation of TFEL (thin film electroluminesence) displays with full color, bright phosphors, which at present would use ZnS-based technology. The drawback with ZnS is that the blue efficiency is too low. With $MGa_2S_4$-based materials, the sputtered films are amorphous, and the crystallization temperature is too high for inexpensive glass, thereby necessitating the use of expensive quartz. The instant invention secures the advantage of not depositing amorphous material in a two-step process. Rather a one-step process is used to get crystalline material directly, thereby providing a superior route to $MGa_2S_4$ in that it has the potential to give significantly higher quality films at dramatically reduced cost. It is unusual to need a metal sulfide composition for an electronic device, and no prior work has been done in the chemical vapor deposition of these materials. Traditionally, chemical vapor deposition methods would exclude sulfur (a dopant). In the instant application, it is included due to its requirement in the target phosphor composition.

While barium bis(2-(2-butoxyethoxy)ethylthiolate) has been described as one specific example of the type of compounds which are envisioned to be encompassed within this invention, it is but one of a series of inorganic ligand complexes which are easily synthesized. For example, while barium is shown to be the coordinating metal, other Group II metals, i.e., Be, Mg, Ca, Sr, and Ra are believed to have applicability in this invention. The preferred Group II metals of Ba and Sr being preferred, Ba being the most preferred embodiment.

The coordinating ligands which are effective in this invention are in general, bis(oligoetherthiolate) ligands of general form $^eS(R^1O)_m(R^2)$, wherein $R^1$ is selected from the group consisting of $C_{1-10}$ alkyls, preferably $C_{1-4}$ alkyls, aryl, cycloalkyls of $C_{4-8}$, preferably $C_{5-7}$, unsaturated alkyls of $C_{1-10}$, trialkylsilyl wherein the alkyl substituent is $C_{1-10}$; m is 1–4, preferably 1 to 2, $R^2$ functioning to achieve electroneutrality; and $R^1$ is a difunctional linker of $C_{1-10}$ alkyl, preferably $C_{1-6}$ alkyl, $C_{2-10}$ alkenyl, preferably $C_{3-8}$, $C_{6-14}$ aryl, polyaryl of 1–3 aryl rings, cycloalkyls of $C_{3-8}$, preferably $C_{4-7}$, aralkyl of $C_{1-10}$ and alkaryl of $C_{1-10}$, and heteroatom derivatives of the above, wherein the heteroatom is selected from the group consisting of O, N, Si, and transition metals and substituted derivatives of the above, wherein the substitution includes halogens, halogenated alkyls of $C_{1-10}$ alkoxy moieties of $C_{1-10}$ and halogenated alkoxy moieties thereof.

In general, intramolecular stabilization of the Group II metal bis(oligoetherthiolate) moiety may be achieved through dimerization of the complex, through Group II metal—sulfur bonds resulting in molecular orbital stabilization through c-bond delocalization. Therefore, in solution, the preferred embodiment would generically be shown as $[M(S(R^1O)_m(R^2))]_2$ wherein $R^1$, $R^2$, and m are as defined previously, and M is selected from the group consisting of Be, Mg, Ca, Sr, Ba and Ra. In a most preferred embodiment, M is Ba.

Alternative Synthetic Routes

While the synthesis of a Group II metal bis(oligoetherthiolate) complexes has been described by the genetic reaction shown below:

(I) M+2 HSR→M(SR)$_2$+H$_2$ wherein R represents $(OR^1)_m(R^2)$ described previously, it is envisioned that the following synthetic procedures would be equally applicable:

(II) MH$_2$+2 HSR→M(SR)$_2$+2 H$_2$ (II) MR'$_2$+2 HSR→M(SR)$_2$+2 R'H wherein R' is any moiety less acidic than RS wherein exemplary R' moieties would include cyclopentadienyl, alkyl, dialkylamide, etc.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. An organosoluble Group II biv(thiolate) compound of general formula $M(S(R^1O)_m(R^2))_2$ wherein M is selected from the group consisting of Be, Mg, Ca, Sr, Ba and Ra;

$R^2$ is selected from the group consisting of $C_{1-10}$ alkyls, aryl, $C_{4-8}$ cycloalkyls, $C_{1-10}$ unsaturated alkyls, trialkylsilyl wherein the alkyl substituent is $C_{1-10}$;

m is an integer from 1 to 4; and $R^1$ is a linker of $C_{1-10}$ alkyl, $C_{2-10}$ alkenyl, $C_{6-14}$ aryl, polyaryl moieties of 2–3 aryl rings, cycloalkyls of $C_{3-8}$, $C_{1-10}$ aralkyl, $C_{1-10}$ alkaryl, heteroatom derivatives thereof wherein the heteroatom is selected from the group consisting of O, N, Si, and transition metals, and substituted derivatives thereof wherein the substituents are selected from the group consisting of halogens, halogenated alkyls of $C_{1-10}$, alkoxy moieties of $C_{1-10}$ and halogenated alkoxy moieties of $C_{1-10}$.

2. The compound of claim 1 wherein $R^2$ wherein $R^2$ is selected from the group consisting of $C_{1-14}$ alkyls, $C_{5-7}$, cycloalkyls, and $C_{1-10}$ unsaturated alkyls; m is an integer from 1 to 2; and $R^1$ is a linker of $C_{1-6}$ alkyl, $CF_{3-8}$ alkenyl, aryl, $C_{1-10}$ aralkyl and $C_{1-10}$ alkaryl.

3. The compound of claim 2 wherein M is selected from the group consisting of barium and strontium.

4. The compound of claim 3 wherein M is barium.

5. The compound of claim 4 wherein the compound is barium bis(2-(2-butoxyethoxy)ethylthiolate).

6. An organosoluble Group II bis(thiolate) compound of general formula $M(S((R^1O)_m(R^2))_2\ 2))2$ wherein M is a Group II metal selected from the group consisting of Be, Mg, Ca, Sr, Ba and Ra;

$R^2$ is an organic moiety selected to achieve charge neutrality of a thiolate ligand;

m is an integer from 1 to 4; and $R^1$ is an Organic moiety capable of forming an oligoether ligand capable of coordination bonding with both the Group II metal and sulfur, the sulfur further stabilizing the compound through dimerization of the complex through the Group II metal—sulfur bonds resulting in molecular orbital stabilization through π-bond delocalization.

7. The compound of claim 6 wherein M is selected from the group consisting of barium and strontium.

8. The compound of claim 7 wherein M is barium.

* * * * *